(12) United States Patent
Wachendorff-Neumann

(10) Patent No.: US 6,436,988 B1
(45) Date of Patent: Aug. 20, 2002

(54) USE OF 3-(2,4,6-TRIMETHYLPHENYL)-4-NEOPENTYLCARBONYLOXY-5,5-TETRAMETHYLENE-$\Delta^3$-DIHYDROFURAN-2-ONE FOR CONTROLLING THE WHITE FLY

(75) Inventor: Ulrike Wachendorff-Neumann, Neuwied (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/889,470

(22) PCT Filed: Jan. 14, 2000

(86) PCT No.: PCT/EP00/00257

§ 371 (c)(1),
(2), (4) Date: Jul. 1, 2001

(87) PCT Pub. No.: WO00/42850

PCT Pub. Date: Jul. 27, 2000

(30) Foreign Application Priority Data

Jan. 20, 1999 (DE) .......................... 199 01 943

(51) Int. Cl.[7] ..................... A61K 31/335; A61K 31/34
(52) U.S. Cl. ...................................... 514/462
(58) Field of Search .................................. 514/461, 462

(56) References Cited

U.S. PATENT DOCUMENTS 5,262,383 A * 11/1993 Fischer et al. .............. 504/195

FOREIGN PATENT DOCUMENTS

EP 0 528 156 2/1993

OTHER PUBLICATIONS

*A.R. Horowitz, G. Rorer & I. Ishaaya: "Mananging resistance in Bemisia tabaci in Israel with Emphasis on cotton." Pestic. Sci., Bd. 42, Nr. 2, Oct. 1994, Seiten 113–122, XP000882657.

* cited by examiner

*Primary Examiner*—Minna Moezie
*Assistant Examiner*—Mojdeh Bahar
(74) *Attorney, Agent, or Firm*—Joseph C. Gil

(57) ABSTRACT

The present application relates to the use of 3-(2,4,6-trimethylphenyl)-4-neopentylcarbonyloxy-5,5-tetramethylene-$\Delta^3$-dihydrofuran-2-one for controlling insects of the family Aleurodidae (white fly).

15 Claims, No Drawings

USE OF 3-(2,4,6-TRIMETHYLPHENYL)-4-NEOPENTYLCARBONYLOXY-5,5-TETRAMETHYLENE-$\Delta^3$-DIHYDROFURAN-2-ONE FOR CONTROLLING THE WHITE FLY This application is a 371 of PCT/EP00/00257 filed Jan. 14, 2000.

FIELD OF THE INVENTION

The present application relates to the use of 3-(2,4,6-trimethylphenyl)-4-neopentylcarbonyloxy-5,5-tetramethylene-$\Delta^3$-dihydrofuaran-2-one for controlling insects of the family Aleurodidae (white fly).

DETAILED DESCRIPTION

The compound 3-(2,4,6-trimethylphenyl)-4-neopentylcarbonyloxy-5,5-tetramethylene-$\Delta^3$-dihydrofuaran-2-one is known from EP-A-0 528 156.

Furthermore, EP-A-0 528 156 discloses that 3-(2,4,6-trimethylphenyl)-4-neopentylcarbonyloxy-5,5-tetramethylene-$\Delta^3$-dihydrofuran-2-one has insecticidal action.

Surprisingly, it has now been found that 3-(2,4,6-trimethylphenyl)-4-neopentyl-carbonyloxy-5,5-tetramethylene-$\Delta^3$-dihydrofuran-2-one is particularly suitable for controlling insects of the family Aleurodidae (white fly) and additionally has considerably better action than the constitutionally most similar compounds known from EP-A-0 528 156.

The present invention accordingly relates to the use of 3-(2,4,6-trimethylphenyl)-4-neopentylcarbonyloxy-5,5-tetramethylene-$\Delta^3$-dihydrofuaran-2-one for controlling insects of the family of the Aleurodidae (white fly).

3-(2,4,6-Trimethylphenyl)-4-neopentylcarbonyloxy-5,5-tetramethylene-$\Delta^3$-dihydrofuran-2-one has the following formula (I):

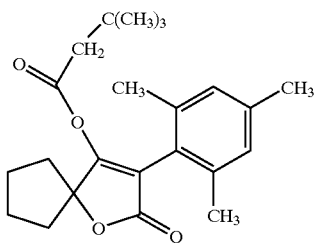

(I)

The compound of the formula (I) can preferably be employed for controlling insects of the genera Bemisia, Trialeurodes, Aleurotrixus, Allurodes, Dialeurodes and Aleurocanthus. The following species may be mentioned by way of example: *Trialeurodes vaporariorum, Bemisia tabaci, Aleurotrixus floccosus* and *Aleurodes brassicae*.

In principle, the compound of the formula (I) can be used in a large number of crops, preferably in cotton, vegetables (for example tomato, aubergines, beans, cucumbers, courgettes, capsicum, melons), ornamental plants, tobacco and citrus plants.

The active compound of the formula (I) can be converted into the customary formulations, such as solutions, emulsions, wettable powders, suspensions, powders, dusts, pastes, soluble powders, granules, suspoemulsion concentrates, natural and synthetic materials impregnated with active compound, and very fine capsules in polymeric substances.

These formulations are produced in a known manner, for example by mixing the active compound with extenders, that is liquid solvents and/or solid carriers, optionally with the use of surfactants, that is emulsifiers and/or dispersants and/or foam-formers.

If the extender used is water, it is also possible to employ for example organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane, or paraffins, for example mineral oil fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize crops and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc, The formulations in general contain between 0.1 and 95% by weight of active compound, preferably between 0.5 and 90%, and additionally preferably extenders and/or surfactants.

The active compound content of the use forms prepared from the commercial formulations can be varied within wide ranges. The concentration of active compound in the use forms can be from 0.0000001 to 95% by weight of active compound, and is preferably between 0.0001 and 1% by weight.

Application is carried out in a customary manner adapted to the use forms.

Preparation of the Compound of the Formula (I)

5.45 g (20 mmol) of 3-(2,4,6-trimethylphenyl)-4-hydroxy-5,5-tetramethylene-$\Delta^3$-dihydrofuran-2-one (known from EP-A-0 528 156) are initially charged in 80 ml of dichloromethane, 3.04 g (30 mmol) of triethylamine are added and, at 0–10° C., a solution of 3.50 g (26 mmol) of 3,3-dimethylbutyryl chloride in 20 ml of dichloro-methane is then added dropwise.

After 2 hours, a further 0.50 g (5 mmol) of triethylamine and 0.40 g (3 mmol) of acid chloride are added, and the mixture is stirred at room temperature for a further 16 hours.

For work-up, the mixture is washed twice with 10% strength citric acid and twice with 1N aqueous sodium hydroxide solution, and the organic phase is dried with sodium sulphate and concentrated.

Further purification of the crude product is effected by trituration with petroleum ether, filtration with suction and drying.

Yield: 4.50 g of a white solid (61% of theory) of melting point: 98° C.

USE EXAMPLE

Bemisia Test

Solvent: 7.5 parts by weight of dimethylformamide
Emulsifier: 2.5 parts by weight of alkylaryl polyglycol ether To produce a suitable preparation of active compound, 1 part by weight of active compound is mixed with the stated amounts of solvent and emulsifier, and the concentrate is diluted with water to the desired concentrations.

Cotton plants (Gossypium hirsutum) infested by eggs, larvae and pupae of the white fly Bemisia tabaci are dipped into a preparation of active compound of the desired concentration.

After the desired period of time, the kill in % is determined. 100% means that all animals have been killed; 0% means that none of the animals have been killed.

TABLE plant-damaging insects
Bemisia test

| Active compounds | Concentration of active compound in % | Kill in % after 14 days |
|---|---|---|
| Compound known from EP-A-0 528 156 | 0.0008 | 50 |

TABLE-continued plant-damaging insects
Bemisia test

| Active compounds | Concentration of active compound in % | Kill in % after 14 days |
|---|---|---|
| Compound known from EP-A-0 528 156 | 0.0008 | 0 |
| Compound known from EP-A-0 528 156 | 0.0008 | 0 |
| Compound of the formula (I) to be used according to the invention | 0.0008 | 95 |

What is claimed is:
1. A method for controlling insects of the family Aleurodidae, comprising the step of applying a composition comprising a compound of the formula (I)

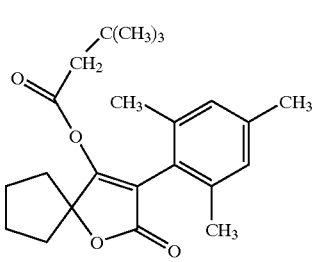

(I)

to insects of the family Aleurodidae and/or their habitats.

2. A method according to claim 1, wherein the composition comprises a compound of formula (I) and an ingredient selected from the group consisting of extenders, surfactants, adhesives, colorants and combinations thereof.

3. A method according to claim 1, wherein the composition is in the form of a concentrate which is diluted before use.

4. A method according to claim 1, wherein the composition comprises between 0.0000001% and 95%, by weight, compound of formula (I).

5. A method according to claim 1, wherein the composition comprises between 0.0001% and 1%, by weight, compound of formula (I).

6. A method according to claim 1, wherein the composition is in a form selected from the group consisting of solutions, emulsions, wettable powders, suspensions, powders, dusts, pastes, soluble powders, granules, suspoemulsion concentrates, and impregnated natural and synthetic materials.

7. A method according to claim 1, wherein the insects of the family Aleurodidae are selected from the group consisting of the genera Bemisia, Trialeurodes, Aleurotrixus, Allurodes, Dialeurodes, Aleurocanthus and combinations thereof.

8. A method for controlling insects of the family Aleurodidae, comprising the step of applying a composition comprising 3-(2,4,6-trimethylphenyl)-4-neopentylcarbonyloxy-5,5-tetramethylene-$\Delta^3$-dihydrofuran-2-one to plants.

9. A method according to claim 8, wherein the composition comprises 3-(2,4,6-trimethylphenyl)-4-neopentylcarbonyloxy-5,5-tetramethylene-$\Delta^3$-dihydrofuran-2-one and an ingredient selected from the group consisting of extenders, surfactants, adhesives, colorants and combinations thereof.

10. A method according to claim 8, wherein the composition is in the form of a concentrate which is diluted before use.

11. A method according to claim 8, wherein the composition comprises between 0.0000001% and 95%, by weight, 3-(2,4,6-trimethylphenyl)4-neopentylcarbonyloxy-5,5-tetramethylene-$\Delta^3$-dihydrofuran-2-one.

12. A method according to claim 8, wherein the composition comprises between 0.0001% and 1%, by weight, 3-(2,4,6-trimethylphenyl)-4-neopentylcarbonyloxy-5,5-tetramethylene-$\Delta^3$-dihydrofuran-2-one.

13. A method according to claim 8, wherein the composition is in a form selected from the group consisting of solutions, emulsions, wettable powders, suspensions, powders, dusts, pastes, soluble powders, granules, suspoemulsion concentrates, and impregnated natural and synthetic materials.

14. A method according to claim 8, wherein the plants are selected from the group consisting of cotton, vegetables, ornamental plants, tobacco, citrus plants and combinations thereof.

15. A method according to claim 8, wherein the insects of the family Aleurodidae are selected from the group consisting of the genera Bemisia, Trialeurodes, Aleurotrixus, Allurodes, Dialeurodes, Aleurocanthus and combinations thereof.

* * * * *